United States Patent [19]

Srinivas

[11] 4,240,472
[45] Dec. 23, 1980

[54] APPARATUS FOR CLEANING AND COATING CAPILLARY TUBES USEFUL IN GAS CHROMATOGRAPHY

[76] Inventor: Srivas R. Srinivas, 2850 Webb Ave., Apt. 5J, Bronx, N.Y. 10468

[21] Appl. No.: 898,776

[22] Filed: Apr. 21, 1978

Related U.S. Application Data

[60] Division of Ser. No. 681,604, Apr. 29, 1976, Pat. No. 4,086,051, which is a continuation of Ser. No. 495,500, Aug. 7, 1974, abandoned, which is a division of Ser. No. 232,583, Mar. 7, 1972, Pat. No. 3,831,555.

[51] Int. Cl.³ .............................................. B63B 31/02
[52] U.S. Cl. ........................................ 141/59; 141/91
[58] Field of Search ................... 137/205, 238; 141/1, 141/7, 18, 31, 59, 89, 91, 92, 97, 285, 383; 222/148; 134/102

[56] References Cited

U.S. PATENT DOCUMENTS

| | | | |
|---|---|---|---|
| 2,548,987 | 4/1951 | Mayo | 141/59 |
| 3,078,685 | 2/1963 | Flournoy | 141/7 X |
| 3,464,464 | 9/1969 | Laub | 141/59 |

*Primary Examiner*—Frederick R. Schmidt
*Attorney, Agent, or Firm*—Rocco S. Barrese

[57] ABSTRACT

An integral system contained in a suitable housing which includes means for coating particulate support material with stationary phase chemicals, means for draining liquid from the coated support material, means for drying the coated support material, and means for transferring the dried, coated support material into a gas-chromatography column. Means for cleaning and coating capillary tubes is also disclosed. Additionally means for conditioning packed columns and capillary tubes is disclosed.

2 Claims, 5 Drawing Figures

APPARATUS FOR CLEANING AND COATING CAPILLARY TUBES USEFUL IN GAS CHROMATOGRAPHY

This is a division of application Ser. No. 681,604 filed Apr. 29, 1976, now U.S. Pat. No. 4,086,051, which in turn is a continuation of application Ser. No. 495,500 filed Aug. 7, 1974, now abandoned, which in turn is a division of application Ser. No. 232,583, filed Mar. 7, 1972, now U.S. Pat. No. 3,831,555.

BACKGROUND OF INVENTION

In the art of gas-liquid chromatography (GLC), it is necessary to prepare packed columns as well as coated capillary tubes which are employed in conjunction with a suitable detector instrument, gas chromatograph, for obtaining analytical data relative to chemical compositions of a highly complex organic substance e.g., essential oils, perfumes, flavors, etc. The preparation of a packed column involves firstly, coating a suitable particulate packing support with a layer of stationary phase chemical, drying the coated support, and then transferring the coated and dried packing into a column of desired dimension in a manner such that the packing material is uniformly or homogeneously distributed throughout the column. The preparation of capillary tubes involves firstly, cleaning a tube with various solutions and then coating the walls thereof with a layer of stationary phase chemical.

In the case of gas-solid chromatography (GSC), the wide bore columns of desired dimension are packed with an inert solid support, such as, Chromosorb porous polymer beads.

Various packing supports and stationary phase chemicals are well known in the gas chromatography art. Typical packing supports include inert materials such as diatomaceous earths, glass beads, polymer beads, crushed fire brick and the like. Stationary phase chemicals include polyesters, polyethylene glycols, methyl and phenyl silicones, substituted silicones as well as many other chemicals.

Various techniques and devices are known in the prior art for performing individual steps involved in the preparation of columns and capillary tubes. For example, U.S. Pat. No. 3,513,562 describes a fluidized drying device for drying coated packing support materials. The use of capillary tubes coated with stationary phase materials is described in U.S. Pat. No. 2,900,478. Vibrating devices, for example, are known for the purpose of assisting in the uniform packing of gas chromatography (GC) columns. While the various prior methods and means are operable to produce packed columns and capillary tubes which may perform adequately for many applications, there has remained a need to maximize efficiency of the entire procedure for preparation of columns and capillary tubes such that the time and expense of preparing such means for use in gas-solid and gas-liquid chromatographic analyses might be substantially reduced. There has also remained prior to this invention a need for preparing packed columns with a very large number of theoretical plates and capillary tubes which will yield more highly consistent and reproducible analytical results.

It is important to properly condition the packed and capillary columns before using them for analysis of the complex mixture of organic compounds. In the prior art, while conditioning the columns, one end of the column is connected to the inlet of the carrier gas whereas the other end is left open to the atmosphere by not connecting it to the detector inlet which otherwise would contaminate the detector system. Thus, in order to meet the aforementioned pre-requisite, very expensive and highly sophisticated gas-chromatograph units are employed thereby increasing the time and expense of preparing such columns for satisfactory use in gas-solid and gas-liquid chromatography. Hence, there has been a great need for a column pre-conditioning means that would be more efficient, and economical to achieve this desired end.

BRIEF DESCRIPTION OF THE INVENTION

In accordance with the present invention a system is provided which is useful for the coating of the particulate support material with stationary phase chemicals, drying or preconditioning the coated support and transferring the prepared coated support material into the GC column in an efficient and highly satisfactory manner. The integrated means of the present invention is also useful for cleaning and coating of capillary tubes employed in GLC analysis as well as in packing the columns with porous polymer solid supports such as Chromosorb polymer beads used in gas-solid chromatography.

The system comprises the following basic and essential elements. Firstly, a housing means is provided to maintain the means hereinafter recited. The housing means will usually include a suitable face panel upon which the various valves, gauges, power switches, pyrometer and flow meters can be placed. The various conduit means, pumps, heater, and other operating parts will preferably be enclosed within the housing.

A first port means is provided which is connected to an extrinsic coating and drying column or to a reservoir for cleaning and coating capillary tubes. The port means are preferably located in the side panel walls of the housing means and the various extrinsic columns, tubes, flasks, etc. are removably connected to the ports but located outside of the housing. Vacuum means such as a conventional vacuum pump is preferably provided in the housing for effecting the various draining, evacuating and transferring operations performed in the preparation of gas chromatography columns and capillary tubes. The vacuum means communicates with the port means through suitable conduit means.

Preferably, the vacuum means is connected to the port through an extrinsic trap flask which can be readily emptied and which is useful in trapping relatively expensive stationary phase chemicals when draining excess solution from a solid support coating operation.

A second port means communicates with the first port means through a first conduit means which is equipped with flow control valves and heating means. When a source of inert gas, e.g., nitrogen gas cylinder, is connected to the second port means, the gas can be passed at a desired temperature and flow rate into the base of a suitable column to dry coated packing or, alternatively, in a stripped-down embodiment of the system of the invention can be connected to a vessel employed for cleaning or coating capillary tubes to force solutions through such capillary tubes.

A second conduit means connected to an extrinsic packing column through third port means communicates with the nitrogen supply port to provide means for transferring coated packing material from the packing column into the gas-chromatography column to be packed.

The above-stated combination of means are capable of effecting the coating, drying packing of wide-bore columns as well as cleaning and coating of capillary tubes in accordance with the system of the present invention. However, the preferred and enlarged system of the present invention is hereinafter described.

It is apparent that the entire preparation of gas-chromatography columns and capillary tubes can be effected in accordance with the present invention with maximum efficiency and minimum handling time. Minimizing handling of support material during the coating and drying operation results in more reproducible, evenly coated and efficient coated supports. In line with this invention very fine particles are readily eliminated and the particular size of the final coated product made more homogeneous. Overall, the columns prepared in accordance with the present invention are found to be superior in analytical performance to columns prepared by prior art methods.

The system of the present invention can also be employed to control the gas supply to a column conditioning unit, and is particularly useful in conjunction with the new column conditioning means hereinafter described.

REFERENCE TO THE DRAWINGS

FIG. 1 of the drawings illustrates diagrammatically, in elevation, one preferred embodiment of the system of the present invention.

DETAILED DESCRIPTION OF INVENTION

Figure 1:
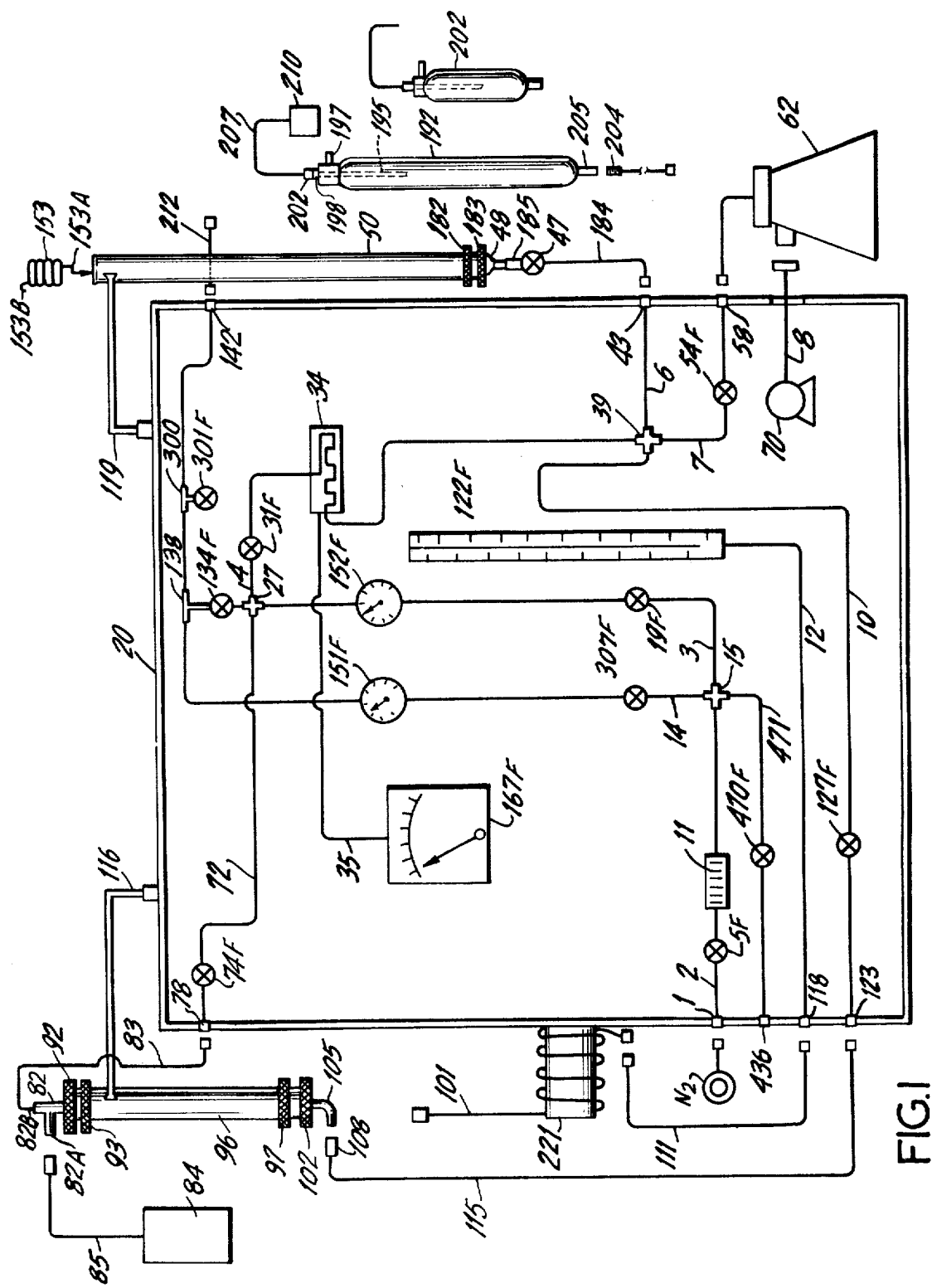

The invention is hereinafter described in detail with reference made to FIGS. 1 thru 5 of the drawings. Housing 20 which can be made of metal, wood or plastic forms a container for the system hereinafter described. For example, a housing 30-inches high, 24-inches wide and 10-inches deep is suitable.

Port 1 serves as an inlet for nitrogen or other inert gas to conduit 2. Port 1 is preferably situated flush with the left side panel of housing 20. Conduit 2 is made of any suitable metal, plastic or ceramic material. For example, copper tubing ⅛-inch in diameter is satisfactory for all conduits. Valve 5F is provided in conduit 2 to control the flow of inert gas which, for example, can be provided by a nitrogen cylinder. The control knob of valve 5 is preferably situated on the front panel surface of housing 20. Each item designated in the drawing by "F" following the numeral is, likewise, situated on the front panel surface of housing 20. The ports such as 1, 118, 123, 436 and 78 are preferably situated flush with the left side panel of housing 20 while ports 142, 43 and 58 are flush with the right side panel.

Nitrogen purifier 11, which is preferably equipped with replaceable cartridges, serves to eliminate moisture and oil from commercial grade nitrogen.

Figure 5:
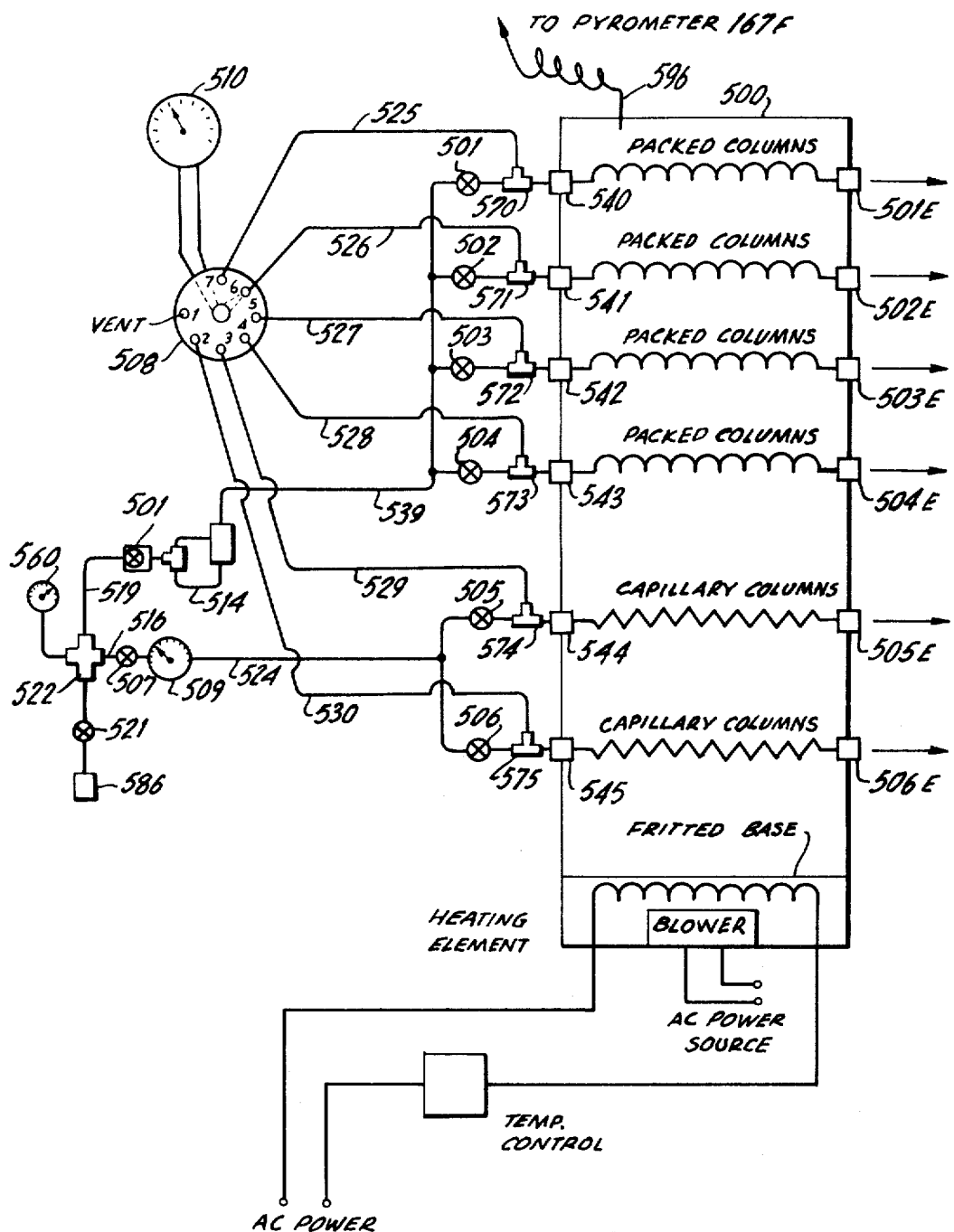
FIG. 5 illustrates diagrammatically, in elevation, novel means useful for conditioning the packed columns and coated capillary tubes prior to using them in a conventional gas chromatography instrument.

Union cross 15 joins conduit 2 to conduits 14, 471 and 3. Auxillary valve 19F is provided in conduit 3 to control the gas supply when drying coated support materials or when cleaning or coating capillary tubes. Auxillary valve 470 F in conduit 471 controls the gas supply to port 436 which can be connected to the conditioning means, e.g. as shown in FIG. 5.

Pressure gauge 152F is provided in conduit 3. This is intended primarily for use when coating and drying solid supports and packing wide-bore columns and is preferably a 0–200 psi gauge. This gauge can also be used for cleaning or coating capillary tubes up to 200 psi. Gauge 152F should be isolated from the high pressure system to prevent damage thereto by closing valves 134F and 19F when 152F is not in use. Union cross 27 renders conduit 4 in open communication with conduits 3 and 72.

Conduit 14 communicating between union cross 15 and port 142 is provided chiefly for use in cleaning capillary tubes when the pressure which is required exceeds about 200 psi. This line may be isolated where such cleaning operation is not performed or eliminated by modification of gauge 152F. Control valve 307F is situated in conduit 14. Pressure gauge 151F is preferably graduated 0–400 psi. Conduit 14 communicates with conduit 3 thru tee 138. Tee 300 and valve 301F are provided for emergency pressure release when employing elevated pressures in conduit 14 for cleaning or coating capillary tubes.

Conduit 4 and control valve 31F are provided to supply nitrogen gas, e.g., for drying coated solid supports. Heating means 34 is provided in combination with pyrometer 167F interconnected by a thermocouple line 35 in order to provide nitrogen gas heated to the desired temperature. Preferred heating means comprises an electrically heated aluminum block around which a stainless steel conduit is wound. In order to improve heat transfer the section of conduit wound around the aluminum block can be reduced in diameter, e.g., from ⅛-inch to about 0.02-inch. A switch (not shown) can be provided on the front panel to regulate the temperature of 34.

Union cross 39 provides a junction point among conduits 4, 6, 10 and 7. Conduit 6 and port 43 are provided, e.g., for coating and drying support material; and also for transferring cleaning solutions into the reservoir 192. Conduit 7, valve 54F and port 58 are provided as drain and evacuation means. Conduit 10, valve 127F and port 123 are provided for use in loading the pack tube 96 with coated support material.

Vacuum pump 70 which is connected to an electric power source and line 8 which can be a heavy gauge flexible tubing or the like are preferably provided as part of the system for use in draining, loading, charging reservoir 192 and evacuating operations. A switch (not shown) can be provided on the front panel of the housing to actuate pump 70.

Conduit 12 which communicates between port 118 and gas-flow meter 122 is provided, e.g., for use in conjunction with packing a gas-chromatography column with Chromosorb polymer beads or with coated packing support material or for measuring the flow rate through the columns being conditioned.

Conventional vibrator 221 is preferably attached to the side panel of housing 20 for use in packing a gas-chromatography column. A switch (not shown) can be provided on the front panel to actuate 221.

Adjustable clamps 116 and 119 can be provided attached to the top of the housing 20 for the purpose of holding-in-place columns such as 50 and 96 employed in the coating and packing procedures as hereinafter described.

Figures 2, 3, 4:
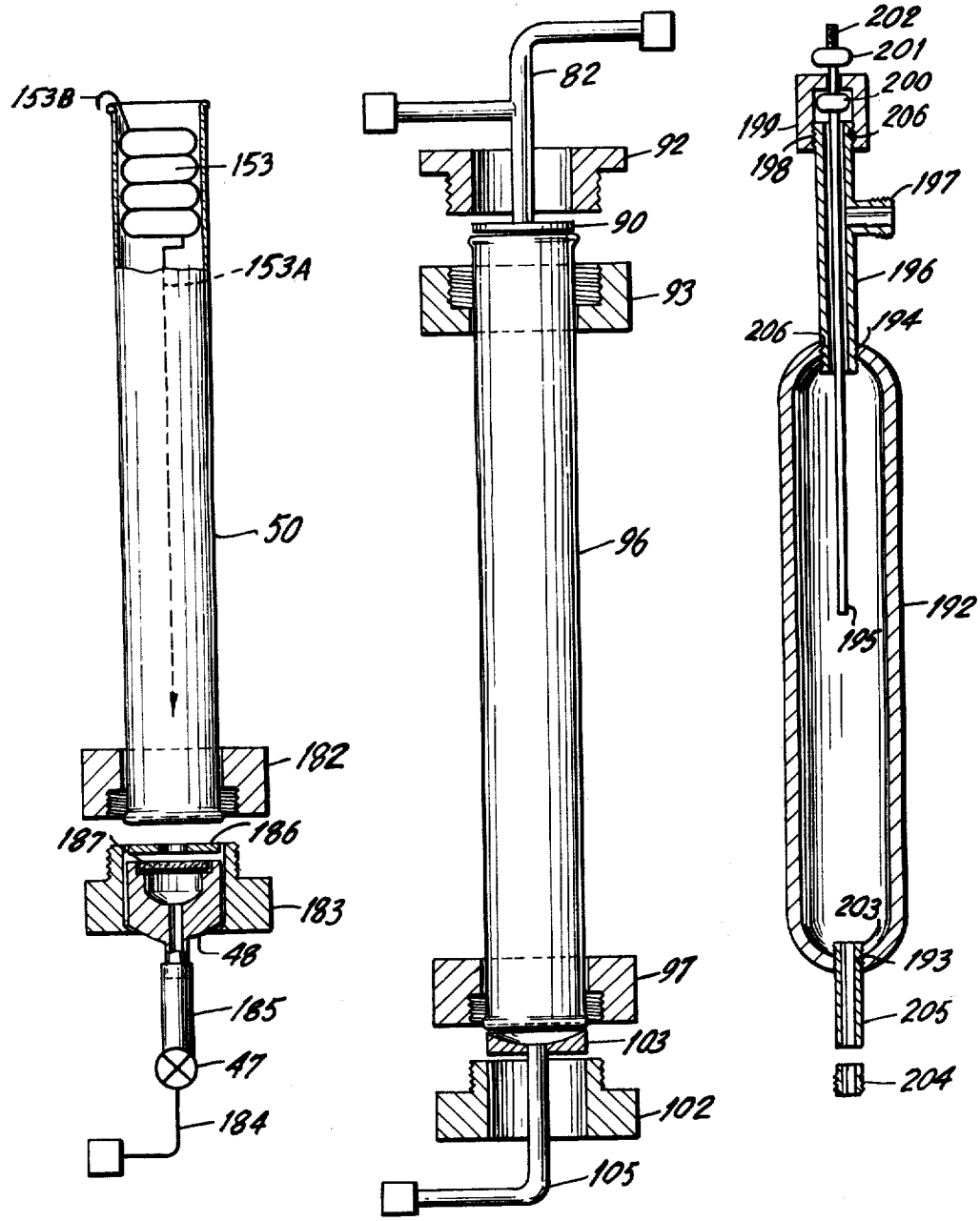
FIG. 2 illustrates a novel and preferred column reservoir useful in preparation of coated packing supports.
FIG. 3 illustrates a novel and preferred column reservoir useful in packing gas chromatography columns.
FIG. 4 illustrates diagrammatically, in elevation, novel means useful for cleaning capillary tubes in conjunction with the system of the present invention.

FIG. 2 illustrates a reservoir assembly useful in coating and drying solid support materials. Glass tube 50, e.g., is heavy, borosilicate glass 24" high and 1" inside diameter. Female-threaded knurled aluminum ring 182 fits snugly around tube 50 and male threaded knurled aluminum ring 183 fits snugly around glass funnel 48. They are assembled by screwing the threads of 183 into 182. The base of tube 50 then holds washer 186 snugly in place which, in turn, holds a removable, porous disc 187 made of sintered glass or any other suitable material firmly against the lip of the glass funnel. Flexible hose 185 is connected to the base of funnel 48 and valve 47, e.g., by means of screw clamps disposed at each end thereof. Copper tubing 184 connects the reservoir assembly with port 43.

Coil 153 is a thin-walled stainless steel tubing ($\frac{1}{8}$" O.D.) coiled and then flattened along the coil and adapted to be inserted into glass tube 50 for use in drying the coated material. The upper end 153B is shaped as a hook to fit over the upper end of 50. The bottom part 153A extends into the bottom portion of tube 50. The function of this device is hereinafter described with reference to drying coated packing material.

FIG. 3, illustrates a novel and preferred reservoir assembly for use in transferring coated or uncoated packing support material into a wide-bore gas chromatography column. Elongated tube 96 made of heavy, borosilicate glass or other suitable material rated to withstand a pressure of 200 psig is fitted at each end with female-threaded knurled aluminum rings 93 and 97. Tube 96, e.g., is 18-inches high and 1-inch inside diameter. A circular plate 103 having an outside diameter such that it fits snugly into the base of tube 96 is rigidly connected to elbow 105. Plate 103 is machined to provide a plano-concave surface which aids in preventing the coated support material transferred into tube 96 from being crushed and fragmented while packing GC-column 101. When male threaded aluminum ring 102 engages 97, plate 103 is held snugly in place and provides a base for the assembly.

Flat plate 90 having a bent tee 82 rigidly connected thereto is held in place by engaging male-threaded knurled aluminum ring 92 with 93 the female threaded knurled aluminum ring.

FIG. 4 illustrates novel means useful, e.g., for cleaning and coating capillary tubes. Elongated thick-walled cylinder 192 capable of withstanding elevated pressures up to about 2,000 psi is adapted with threaded ends 194 and 193. Conduit 205 having threads 203 and 204 cut in each end thereof engages threads 193 at the bottom of the cylinder. Tee-shaped conduit 196 engages threads 194 at the top of the cylinder through threads 206. Dip tube 195 is removably secured to the top of 196 at threads 198 by means of threads 206 cut in nut 199 which is rotatably mounted on dip tube 195. Protruberances 201 and 200 restrain axial movement of nut 199 on 195. Threads 202 are provided at the top of 195 for making further connections to auxiliary means. The operation of this assembly is described with reference to procedure for cleaning and coating capillary tubes. The dip tube 195 is designed to transfer corrosive cleaning liquids such as nitric and nitrous acids, ammonium and sodium hydroxides, etc., into cylinder 192 with great care and without danger to the analyst or to objects in the laboratory working area. All fittings are designed to give pressure-tight operation at about 1500 psi. Cylinder 192 is made of stainless steel. Although a cylinder of 150 to 500 cc capacity can be used, a cylinder of about 300 cc capacity is preferred for cleaning capillary tubes. For coating capillary tubes a cylinder with 10 to 100 cc capacity could be employed, but a cylinder with 50 cc capacity is most desirable for this purpose.

FIG. 5 illustrates novel means useful for conditioning the packed and capillary columns. This device includes an oven that can be electrically heated up to 500° C. and equipped with connections for suspending wide bore packed columns and capillary columns simultaneously in the oven. Means are also provided to ascertain the packing density by measuring the column back pressure at any chosen temperature during conditioning which should later enable the analyst to choose the optimum flow settings on a conventional gas chromatograph without going through the tedious and time consuming procedure of flow rate calibration. Necessary fittings for connecting packed columns of $\frac{1}{8}$" to $\frac{1}{2}$" diameter tubings up to 50 feet in length and capillary columns up to 1000 feet in length to the gas supply and to the flow measurement devices are provided. The oven chamber is so designed that columns of every conceivable shape such as straight biwalled columns, hair pin or folded hair pin, pan cake, helical or randomly coiled to 10" in diameter used in the gas chromatographic analyses of complex organic mixtures can be accomodated readily. Housing 500 which is preferably made of metal forms a container for the system hereinafter described. For example, a thermally insulated steel housing 36" high, 24" wide and 12" deep is suitable from an economic point of view. This will accomodate four packed wide bore columns and two capillary columns each up to 50 feet and 1000 feet in length respectively.

Ports 540, 541, 542, 543, 544 and 545 serve as inlets for nitrogen or other inert gas to individual columns. Ports 501E, 502E, 503E, 504E, 505E and 506E serve as the outlet fittings for the exit end of the columns.

All ports, 540 to 545 and 501-E to 506-E are preferably situated flush with the left side and right side panels of the housing 500.

The conditioning unit is connected to the unit contained in housing 20 by connecting port 586 at the terminal part of conduit 521 to port 436. Union cross 522 connects pressure gauge 560, inlet conduit 521, and conduits 519 and 516. Gauge 560 is preferably graduated 0–200 psi and permits measurement of the gas inlet pressure.

Conduit 519 is in communication with conduit 539 through valve 501 and flow controller 514.

Conduit 539 supplies inert gas to individual ports 540 thru 543. Valves 501, 502, 503 and 504 are provided to control the gas supply to individual columns connected to the ports 540, 541, 542 and 543, respectively.

Tees 570 through 573 situated at the positions indicated in FIG. 5 connect the respective valves to the column inlet ports and are also in communication with the rotary valve 508 through the corresponding conduits 525, 526, 527, and 528. Rotary valve 508 is a conventional rotary valve, e.g., as made by R. S. Crum Co., for connecting any one of conduits 525 thru 530, to pressure gauge 510.

Conduit 516 is in communication with conduit 524 which supplies inert gas to capillary columns connected to the ports 544 and 545 through the respective valve 505 and 506. A pressure regulator e.g., 0 to 50 psi, with a gauge 509 and a control valve 507 is provided in conduit 524 to regulate the gas supply.

Tees 574 and 575 connecting respectively the valve 505 to port 544 and 506 to 545 are in communication with the rotary valve 508 through the respective conduits 529 and 530.

Rotary valve, preferably a 7-way valve, is connected to a pressure gauge, e.g., 0–200 psi, and is in communication with the inlet of the columns through the conduits 525 through 530. Choosing the appropriate positions by means of a knob on the rotary valve enables the analyst to read the back pressure at the inlet of the column which is being conditioned. By placing the knob to the vent position, pressure on the gauge can be released.

Thermocouple lead 590 can be connected to pyrometer 167F within housing 20 to read the temperature of the oven.

Column outlets, 501E, through 506E can be connected to the flow meter 122F on the housing 20 through conduit 111 and port 118. This enables the analyst to determine the flow rate through the column.

PROCEDURE FOR COATING AND DRYING SOLID SUPPORT MATERIAL

Column reservoir 50 is assembled as described with reference to FIG. 2 and is held in place by clamp means 119. Conduit 184 is connected to port 43. Coil 153 is removed during the coating procedure. All valves including valve 47 should be closed. Any desired coating solution is introduced through the open top into 50. A pre-weighed amount of particulate support material is then introduced into the coating solution and permitted to stand undisturbed for a suitable period of time, e.g., 5–20 minutes.

The following procedure is followed only in the case of solution coating technique but omitted when a slurry coating method is used.

The top of tube 50 is preferably closed off once solid support material is added by inserting in the upper part thereof a vertically elongated tube containing a special mixture of oxysorb, ascarite and activated charcoal. This eliminates oxygen moisture, and organic vapors from air entering the system while draining the excess solution.

Drain flask 62 is connected to port 58 and line 8. Vacuum pump 70 is started and valves 54F and 47 are opened to permit draining of solution from tube 50.

When solution is removed from tube 50 leaving wet coated solid material, hose 185 is disconnected from valve 47. The same solvent used for dissolving the stationary phase chemical can be introduced into valve 47, with the vacuum system on, in order to dissolve any stationary phase material, which may be very expensive. The dissolved material is then trapped in flask 62 from which it can be recovered for reuse.

Once the solid support material in tube 50 has been coated, the following procedure is observed to dry the coated support. Pump 70 is turned off and valve 54F is closed. Hose 185 is reconnected to valve 47 and vertically elongated tube is removed from the top of 50. Coil 153 which has been coated with oil or other sticky substance is inserted into tube 50 such that 153A extends well below the surface of the coated support material. Valves 31F and 19F are opened. Nitrogen supply is connected to port 1 and the tank delivery gauge is set to 50–100 psi. Valve 5F is opened slowly until the pressure reading on 152F is, e.g., between about 10–20 psi. The nitrogen gas flows thru purifier 11 and thru heater 34 for elevation in temperature to a desired level for drying the support material in tube 50. Coil 153A prevents the wet cake of coated support material from rising as a mass during the initial drying period. Thereafter the flow of gas upwardly thru porous sintered disc 187, which acts as a sparger or distributor, and the particulate solids tends to fluidize the material in tube 50. The finer particles tend to migrate to the top of tube 50 due to elutriation by the inert gas are trapped on 153 and then discarded. Thus, the particulate support material is made more homogeneous relative to particle size distribution during the drying step in tube 50.

When the support material in tube 50 is dried and free flowing, electric power supply to the heater is turned off and all valves are closed to shut off the gas supply. Tube 50 is disconnected at valve 47 and the coated support material is transferred to a suitable air-tight container for storage until the packing operation. Alternatively, it is contemplated that tube 50 can be employed directly in place of the packing reservoir 96, after assembling the appropriate parts described with reference to FIG. 3.

PROCEDURE FOR PACKING WIDE-BORE COLUMNS

The assembled packing column 96, described with reference to FIG. 3 is held in place by clamp means 116. Line 85 is connected to tee 82 at 82A. The alternate opening 82B is connected to gas supply port 78 by means of connecting line 83. Port 123 is connected to elbow 105 at the base of tube 96 by means of conduit 115. Special connector 108 is packed with stainless steel or glass wool to prevent the coated packing material from being drawn below that point. With all other valves closed, valves 127F and 54F are opened while vacuum pump 70 is started and the precoated and dried support material in the air-tight container 84 is held at the end of line 85. This draws the coated packing support material from container 84 into tube 96.

Once the desired amount of support material whether coated or uncoated has been transferred into 96 the following procedure is employed to pack wide-bore GC columns, e.g., $\frac{1}{8}$–$\frac{3}{4}$-inch outer diameter GC columns with the support material. Line 85 is disconnected from 82A and the opening is closed with a suitable plug. Line 115 is disconnected from 105.

The GC column 101 bent to the desired shape is brought into contact with vibrator 221. One end of this column is connected to 105, while the other end is connected to port 118 by means of conduit 111. Special connector 108 is used between the GC column end and the conduit 111. The nitrogen supply is connected to port 1. By opening valves 5F and 19F the pressure reading on 152F is brought to about 100 psi, for example, which is suitable for packing a column 10 ft. long and $\frac{1}{8}$-inch outer diameter. The vibrator 221 is turned on. With valves 134F and 31F closed, valve 74F is opened causing packing support material to flow from tube 96 into the GC column 101. When the column is packed in a uniform manner the pressure on 152F and the flow reading on 122F become constant and stable. If there is an obstruction in the tube the flow reading on 122F will fall to zero and the pressure shown on 152F will be higher than expected. It is apparent that columns of constant dimension packed with the same coated support material will exhibit the same final flow reading on 122F and pressure on 152F. Thus, the system of this invention permits preparation of highly reproducible and reliable packed columns.

When the gas chromotography column is packed, the vibrator 221 and nitrogen valve 5F are turned off. When the pressure on 152F shows zero the column may be disconnected, conditioned and then connected to a conventional GC detector.

PROCEDURE FOR CONDITIONING COLUMNS

The following procedure is followed to condition the packed columns or coated capillary tubings.

In order to condition the columns or the capillary tubings, one end thereof, preferably, the detector end is connected to any of the inlet ports 540 through 543 for packed columns or 544-545 for the capillary tubings. The other end is connected to one of the exit ports 501-E through 506-E. The oven temperature is set to about 20° C. below the maximum recommended temperature for that particular stationary phase, for example 100° C. The gas supply to the column is then started. In order to obtain an appropriate flow of gas the knob on rotary valve 508 is set to the proper position to read the column inlet pressure on gauge 510. The pressure reading on gauge 510 is then set to an appropriate reading at the proper selected temperature by adjustment of control valve 501, e.g., 40 psi for a 10 feet by ⅛" inches packed column.

The column is conditioned at the temperature chosen for a period of about 2 to 24 hours for packed columns and capillary tubings and perhaps for several days depending upon the purity and homogenity of liquid stationary phase or the inert solid support, such as, chromosorb porous polymer beads and also depending upon whether the columns so prepared are intended for GC-coupled MS-analyses. For example, the column is conditioned at 200° C. for 24 hours with gas flowing through the column.

During the column conditioning period the flow rate at the column exit at any column temperature can be conveniently measured by connecting the column exit to the flow meter 122F through conduit 111 and port 118. Further measurement of the column back pressure at the carrier gas inlet which bears a direct relationship to the flow through the column can be detected by means of gauges 510 or 509.

After the specified period of time, e.g., 24 hours, the oven is cooled to room temperature and the column temperature is reset, e.g., to 100° C. and the pressure reading on gauge 510 is reset to 40 psi. The flow rate at the column exit is measured by connection with 122F. For example, the flow rate is 30 c.c. per minute at 100° C. and 40 psi inlet pressure. The conditioned column can now be removed and transferred to a GC unit. If the inlet pressure is set to 40 psi at a column temperature of 100° C., the flow rate of gas will automatically be 30 cc per minute.

Important features and advantages of the column conditioning unit include the following:

1. Allows the analyst to determine the desired optimum flow rate calibration during the conditioning operation;

2. Abbrogates contamination of components separated by gas chromatography thus more reliable and accurate spectroscopic data, e.g., infra-red and mass spectroscopic data, can be obtained on GC pure materials;

3. Columns conditioned employing the unit described in the present invention ameliorates the results of temperature and flow programmed gas chromatographic analyses;

4. Saves the time of very expensive and highly sophisticated instruments that are otherwise occupied for conditioning columns;

5. Eliminates base line drift during programmed GC-analyses thus improving integration accuracy;

6. The unit can be used for simultaneous conditioning of packed as well as capillary columns of every conceivable shape such as straight, coiled, hairpin, pancake, helical, etc.;

7. Individual column back pressure can be measured during column conditioning by operating a selector valve switch. This not only enables the analyst later to choose the optimum flow settings on a conventional gas chromatograph but also with minimum effort to check the similarity of two columns packed with the same uncoated or coated support;

8. Eliminates the contamination of detectors with the lower molecular weight fragments normally present in the stationary liquid phases that would clute off of the wide bore packed and wall coated capillary columns during conditioning. Constant deposition of such impurities on the detector components would have an adverse effect upon the sensitivity of such detectors, viz., thermal conductivity, flame ionization, electron capture and micro-cross section detectors.

COMPARATIVE ANALYTICAL DATA ON THE PERFORMANCE OF COLUMNS PREPARED ACCORDING TO THE PRESENT INVENTION AND THE KNOWN ART

|  | PRESENT INVENTION | | | KNOWN ART | | |
|---|---|---|---|---|---|---|
|  | $t_R$ | K | R | $t_R$ | K | R |
| alpha-pinene | 16.25 | 54.0 |  | 8.75 | 42.5 |  |
| beta-pinene | 27.50 | 79.0 | 3.0 | 12.50 | 75.0 | 1.6 |
| myrcene | 31.25 | 104.0 | 1.5 | 17.50 | 87.5 | 0.6 |
| limonene | 43.75 | 145.8 | 3.3 | 22.50 | 112.5 | 1.3 |
| gamma-terpinene | 55.00 | 183.3 | 3.6 | 28.75 | 139.5 | 1.5 |
| column length |  | 3000 mm | | | 3000 mm | |
| column diameter (OD) |  | 3.125 mm | | | 3.125 mm | |
| theoretical plates |  | 91,800 | | | 27,880 | |
| HETP |  | 0.032 mm | | | 0.107 mm | |

NOTE:
$t_R$ = Adjusted retention distance (mm)
k = Partition ratio
R = The resolution of two adjacent peaks
HETP = Height Equivalent to Theoretical Plates

PROCEDURE FOR CLEANING AND COATING CAPILLARY TUBES

The following procedure is employed for cleaning and coating capillary tubes, e.g., a stainless steel tubing having 0.0625-inch external diameter and 0.02-inch internal diameter and 250 feet long. It is highly useful in the GC-MS analysis of very complex mixtures of organic compounds such as essential oils and flavors.

In order to clean the capillary tube, one end thereof is connected to conduit 205 and the other end of the capillary tube is closed with a suitable plug. The means shown in FIG. 4 is fully assembled with dip tube 195 in place. Conduit 207 is connected at 202 and the other end thereof is dipped well below the cleaning fluid level in container 210. Spigot 197 is connected to vacuum source, e.g., by means of a suitable connecting conduit communicating between 197 and port 43. Valve 54F is opened after the vacuum pump 70 is turned on and all other valves are closed. When the desired amount of cleaning fluid has been transferred into 192 the vacuum is shut off. Spigot 197 is disconnected from the vacuum conduit and plugged by suitable means. Dip-tube 195 prevents contact of the various surfaces of tee conduit 196 with highly corrosive cleaning fluids and, of course, make disassembly of the cylinder safer for the analyst or technician.

After cleaning fluid has been transferred into 192, dip tube 195 is removed from the top of tee conduit 196 by unscrewing nut 199. One end of conduit 212 is then connected to threads 198 and the other end is connected to high pressure gas supply port 142. The plug employed to close off the outlet end of the capillary column is removed and after making sure all other valves are closed, valves 5F and 307F are opened. The pressure on gauge 151F is adjusted to the desired level depending upon the length and internal diameter of the capillary tube, nature of cleaning solution, etc., e.g., between 100–400 psi such that the flow of nitrogen gas forces solution downwardly from cylinder 192 through the capillary tube. To disrupt the operation at any instant close valve 307F and open valve 301F. This procedure may be repeated as many times as is required to effect cleaning of the capillary tube.

Coating capillary tubes can be accomplished by the same procedure and means hereinabove described except that a suitable coating solution is substituted for the cleaning solution. It is also preferred to employ a smaller cylinder, e.g., as represented by cylinder 220 shown in FIG. 1. While the larger cylinder 192 can be employed for cleaning the capillary tubes, a cylinder of the same design as described with reference to FIG. 4 but having a volume of 10–100 cc is most desirable for performing coating operation.

In the coating procedure a pressure of 50–110 psi, for example, as indicated on gauge 151F is preferred depending upon the physical characteristics of the coating solution and dimensions of the tube to be coated. It is also desirable to continue the flow of nitrogen through the capillary tube at a pressure, e.g., 50 psi, for 12 to 24 hours after the desired quantity of coating solution has been passed through the cleaned capillary tube.

A procedure for dynamic coating of capillary tubes is described in Dijkstra, G., and J. DeGoey, *Gas Chromatography* 1958, D. H. Desty, Editor, Butterworths, London, 1958, p, 56. According to this method a suitable stationary phase is dissolved in a solvent and then passed through the capillary tube. The deposition of stationary phase material on the walls of the capillary tube is governed, among other factors, by the rate of flow of solution through the tube, concentration of stationary phase and other factors related to specific compositions.

The present invention provides means for eliminating physical variables relative to the coating procedure and thereby achieving more reproducible results as well as more efficient preparation of capillary tubes.

Having thus described the invention with reference to specific embodiments thereof many modifications and alterations thereof will become apparent to those skilled in the art without departing from the spirit and scope thereof.

I claim:

1. A device useful for cleaning and coating capillary tubes which comprises: an elongated vessel having walls capable of withstanding elevated pressures up to about 2000 psi, an elongated conduit having an inside open passageway removably inserted into one end of said elongated vessel so as to form a pressure-tight connection therewith, an elongated tube adapted with connection means at one end thereof removably fastened to the upper end of said elongated conduit so as to form a pressure tight connection therewith, said tube depending through the open passageway inside of said conduit and extending into said elongated vessel, means for connecting the top portion of said tube to auxiliary fluid lines, said elongated conduit being adapted with means situated on the side wall thereof for connection to a vacuum line, and means removably insertable into the alternate end of said elongated vessel for forming a pressure tight connection with a capillary tube or the like, wherein a capillary tube is removably inserted in said means removably insertable into the alternate end of said elongated vessel, and wherein a desired amount of cleaning fluid is drawn into said vessel from said elongated tube by connecting said vacuum line connecting means to a vacuum source, and then said vessel is pressurized to flow the cleaning fluid out of the vessel into said capillary tube.

2. The device of claim 1 wherein said capillary tube is stainless steel and has a 0.0625 inch external diameter and 0.02 inch internal diameter.

* * * * *